(12) United States Patent
Jenkins

(10) Patent No.: US 10,278,551 B2
(45) Date of Patent: May 7, 2019

(54) MULTI-PART SKIN CARE BARS AND RELATED METHODS

(71) Applicant: David L. J. Jenkins, Portland, OR (US)

(72) Inventor: David L. J. Jenkins, Portland, OR (US)

( * ) Notice: Subject to any disclaimer, the term of this patent is extended or adjusted under 35 U.S.C. 154(b) by 722 days.

(21) Appl. No.: 14/619,571

(22) Filed: Feb. 11, 2015

(65) Prior Publication Data
US 2015/0230669 A1 Aug. 20, 2015

Related U.S. Application Data

(60) Provisional application No. 61/941,343, filed on Feb. 18, 2014.

(51) Int. Cl.
| | |
|---|---|
| A61K 8/00 | (2006.01) |
| A47K 7/03 | (2006.01) |
| A61K 8/02 | (2006.01) |
| A61Q 19/10 | (2006.01) |
| G06Q 90/00 | (2006.01) |
| C11D 9/20 | (2006.01) |
| C11D 9/22 | (2006.01) |
| C11D 13/28 | (2006.01) |
| C11D 17/04 | (2006.01) |
| A47K 7/02 | (2006.01) |

(Continued)

(52) U.S. Cl.
CPC ............ *A47K 7/03* (2013.01); *A47K 7/028* (2013.01); *A61K 8/0216* (2013.01); *A61K 8/361* (2013.01); *A61K 8/965* (2013.01); *A61Q 19/10* (2013.01); *C11D 9/20* (2013.01); *C11D 9/225* (2013.01); *C11D 13/28* (2013.01); *C11D 17/04* (2013.01); *G06Q 90/00* (2013.01); *A61K 2800/28* (2013.01); *A61K 2800/87* (2013.01); *A61K 2800/88* (2013.01)

(58) Field of Classification Search
USPC .................................................. 510/146, 148
See application file for complete search history.

(56) References Cited

U.S. PATENT DOCUMENTS

| | | | | |
|---|---|---|---|---|
| 4,203,857 A | * | 5/1980 | Dugan ..................... | A47K 7/03 |
| | | | | 15/104.93 |
| 4,996,000 A | * | 2/1991 | Redeker ............... | C11D 17/006 |
| | | | | 510/139 |

(Continued)

*Primary Examiner* — Necholus Ogden, Jr.
(74) *Attorney, Agent, or Firm* — DASCENZO Intellectual Property Law, P.C.

(57) ABSTRACT

A multi-part skin care bar and methods of using the same are disclosed. The multi-part skin care bar may be formed by selectively coupling a first portion from a plurality of first portions with a second portion from a plurality of second portions. For example, a first engagement portion of a respective first portion may be engaged with a second engagement portion of a respective second portion to couple the first portion to the second portion. In some examples, the first engagement portion may include a first projection and a first receiving hole, the second engagement portion may include a second projection and a second receiving hole, the first projection may be configured to be inserted into the second receiving hole, and the second projection may be configured to be inserted into the first receiving hole in order to couple a respective first portion to a respective second portion.

19 Claims, 5 Drawing Sheets

(51) Int. Cl.
*A61K 8/36* (2006.01)
*A61K 8/96* (2006.01)

(56) References Cited

U.S. PATENT DOCUMENTS

| | | | | |
|---|---|---|---|---|
| 5,198,140 | A * | 3/1993 | Joshi | C11D 13/08 |
| | | | | 252/8.84 |
| 6,555,509 | B2 * | 4/2003 | Abbas | A61K 8/02 |
| | | | | 264/251 |
| 7,014,381 | B1 * | 3/2006 | Graham | A47K 7/028 |
| | | | | 401/201 |
| 8,303,203 | B2 * | 11/2012 | Bahash | A47K 5/08 |
| | | | | 401/49 |
| 2006/0178079 | A1 * | 8/2006 | Tsutsui | A47K 5/04 |
| | | | | 446/73 |

* cited by examiner

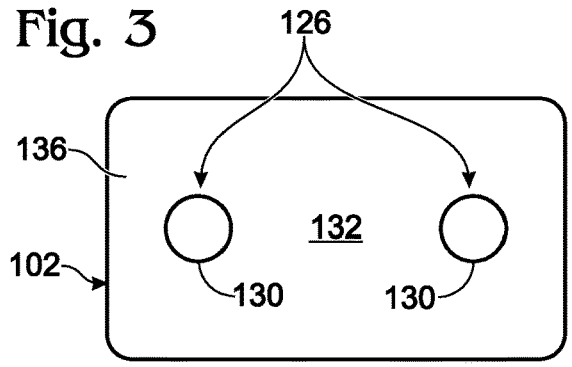
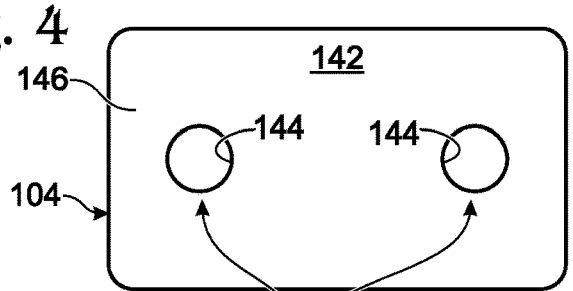
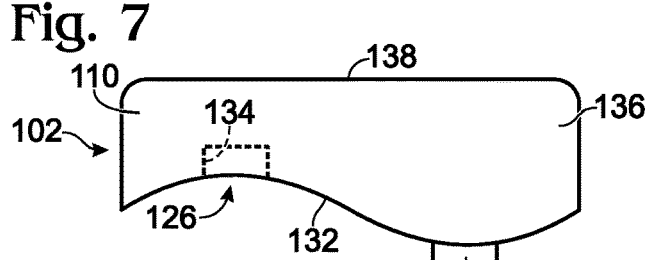
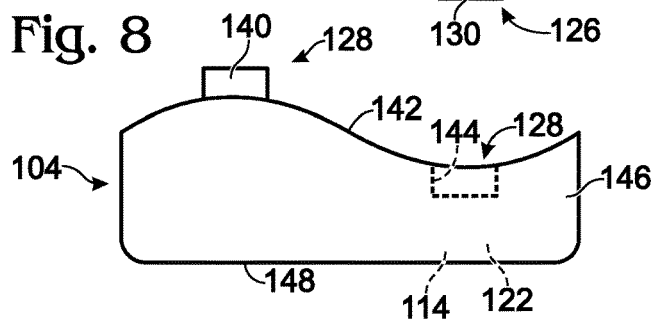
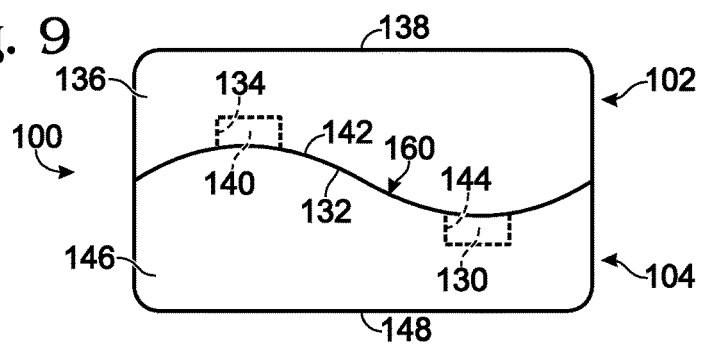

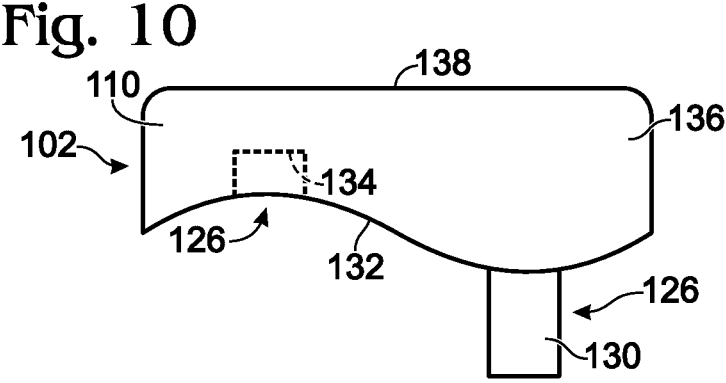
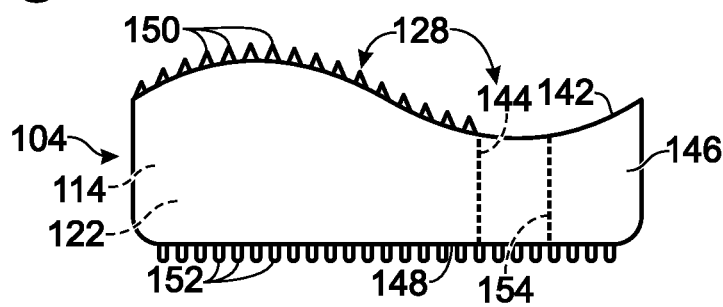
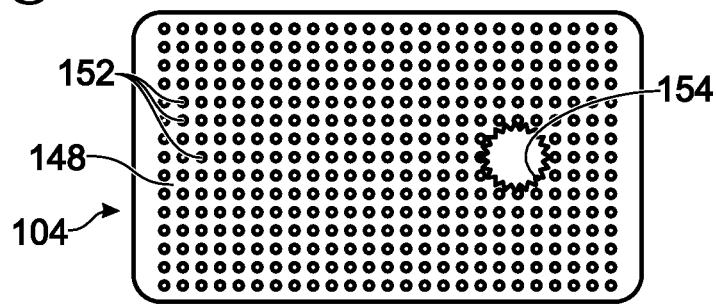
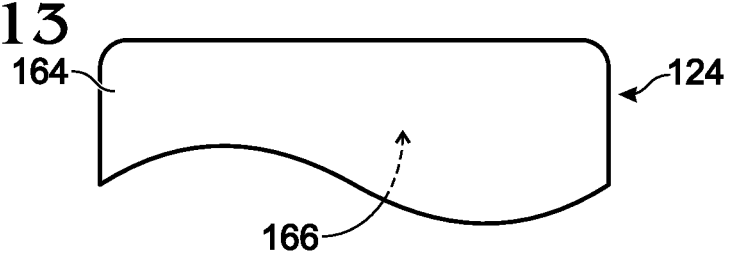

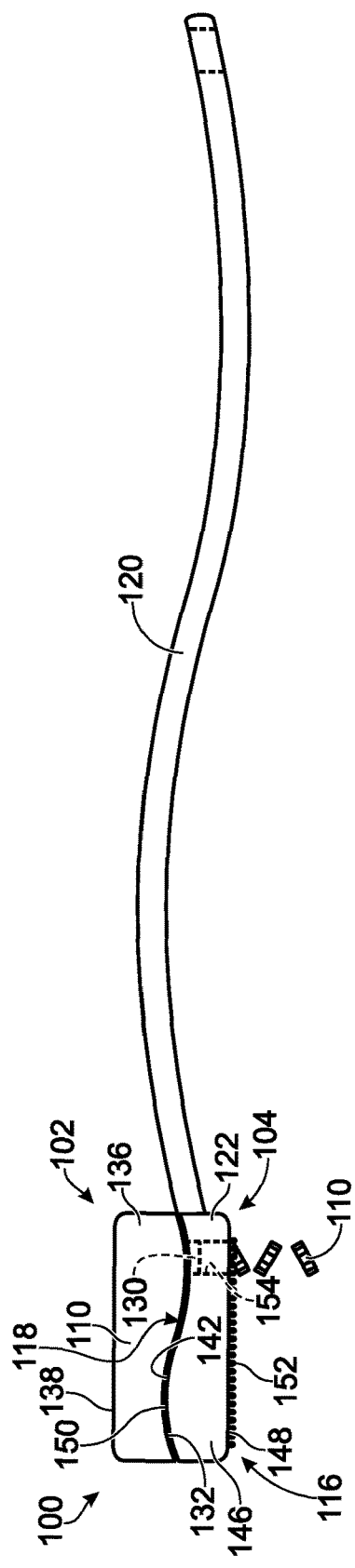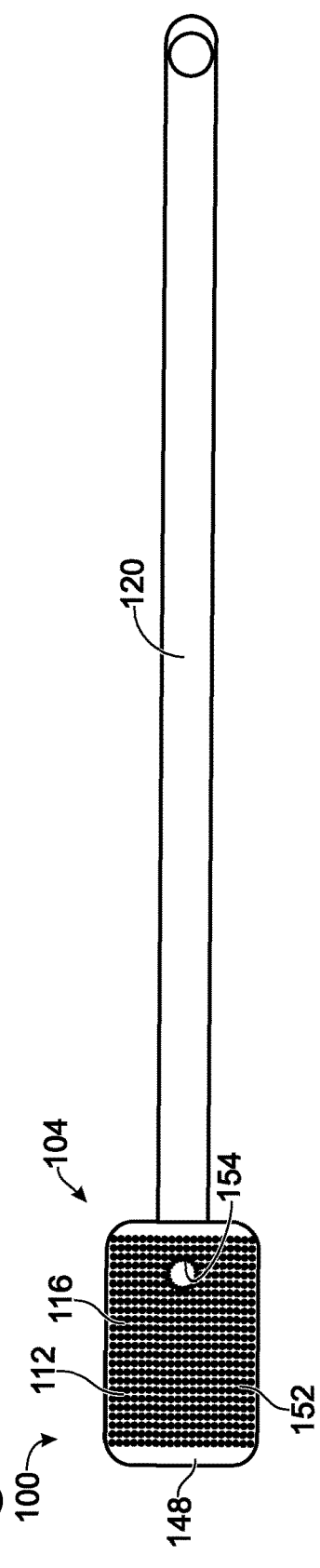

MULTI-PART SKIN CARE BARS AND RELATED METHODS

RELATED APPLICATION

The present application claims priority to U.S. Provisional Patent Application Ser. No. 61/941,343, which was filed on Feb. 18, 2014, and the complete disclosure of which is incorporated by reference.

FIELD

The present disclosure relates to multi-part skin care bars and related methods.

BACKGROUND

Pumice is a porous, textured, volcanic rock, created when super-heated, highly pressurized rock is violently ejected from a volcano. Rapid cooling and depressurization causes volcanic gases to be trapped and unable to escape before the viscous magma chills to volcanic glass, thereby forming the highly porous rock. Pumice, either in bulk form or in a ground form, may be used as an abrasive, in lightweight concrete, in polishes, in pencil erasers, in cleaners, in grease-removing hand soaps, and cosmetic exfoliants. "Pumice stones" are often used in pedicures for removing dry and rough skin from the feet. Several varieties of soap (either liquid or bar soap) include ground pumice as a way to clean dirty hands without the use of harsh cleaning agents or chemicals. Such pumice soaps often are used by gardeners and mechanics. A variety of existing pumice bar soaps have been developed, some with a pumice cleanser on one side of the bar and a regular soap on the other side of the bar. These dual-layer pumice soap bars are fixed and cannot be readily modified before or after purchase. In other words, consumers are unable to customize such existing pumice soaps to their preferences or needs.

SUMMARY

Presently disclosed multi-part skin care bars and related methods may provide users with a customizable skin care bar having two or more parts which may be interchangeable and/or substitutable. For example, a multi-part skin care bar may include a first portion that may be coupled to a second portion to form the multi-part skin care bar. The first portion may be selected from a plurality of first portions, and may include a first body comprising soap, a first surface, and a second surface opposite the first surface, wherein the first surface includes a first engagement portion. The second portion may be selected from a plurality of second portions and may include a second body comprising pumice, pumice soap, and/or plastic, a third surface, and a fourth surface opposite the third surface, wherein the third surface includes a second engagement portion. The first portion and the second portion may be configured to be coupled together via the first engagement portion and the second engagement portion to form the multi-part skin care bar.

Related methods also are disclosed. One method of using a multi-part skin care bar includes selecting a first portion of the multi-part skin care bar, selecting a second portion of the multi-part skin care bar, and forming the multi-part skin care bar by coupling the first portion to the second portion. For example, a first projection on the first portion may be inserted into a second receiving hole formed in the second portion, and a second projection on the second portion may be inserted into a first receiving hole formed in the first portion in order to couple the first portion to the second portion. In some methods, the first portion may be selected from a plurality of first portions (e.g., a plurality of varieties of soap), and the second portion may be selected from a plurality of second portions (e.g., a plurality of varieties of pumice soap).

BRIEF DESCRIPTION OF THE DRAWINGS

FIG. 3 is a bottom plan view of one example of a portion of a multi-part skin care bar according to the present disclosure.

FIG. 4 is a top plan view of another example of a portion of a multi-part skin care bar according to the present disclosure.

FIG. 7 is a side elevation view of an example of a first portion of a multi-part skin care bar according to the present disclosure.

FIG. 8 is a side elevation view of an example of a second portion of a multi-part skin care bar according to the present disclosure.

FIG. 9 is a side elevation view of the first portion of FIG. 7 and the second portion of FIG. 8, shown coupled together according to the present disclosure.

FIG. 10 is a side elevation view of another example of a first portion of a multi-part skin care bar according to the present disclosure.

FIG. 11 is a side elevation view of another example of a second portion of a multi-part skin care bar according to the present disclosure.

FIG. 12 is a bottom plan view of the second portion of FIG. 11.

FIG. 13 is a side elevation view of a cover element for use with a multi-part skin care bar according to the present disclosure.

FIG. 14 is a side elevation view of multi-part elongate scrubber according to the present disclosure.

FIG. 15 is a bottom plan view of the multi-part elongate scrubber of FIG. 14.

DESCRIPTION

The present disclosure concerns multi-part skin care bars, kits containing the same, and related methods. Presently disclosed multi-part skin-care bars may be formed by coupling together two portions, where each of the portions may be selected from a plurality of different options, thereby providing a customizable and/or interchangeable multi-part skin care bar. Generally, in the figures, elements that are likely to be included in a given example are illustrated in solid lines, while elements that are optional to a given example are illustrated in broken lines. However, elements that are illustrated in solid lines are not essential to all examples of the present disclosure, and an element shown in solid lines may be omitted from a particular example without departing from the scope of the present disclosure.

Figure 1:
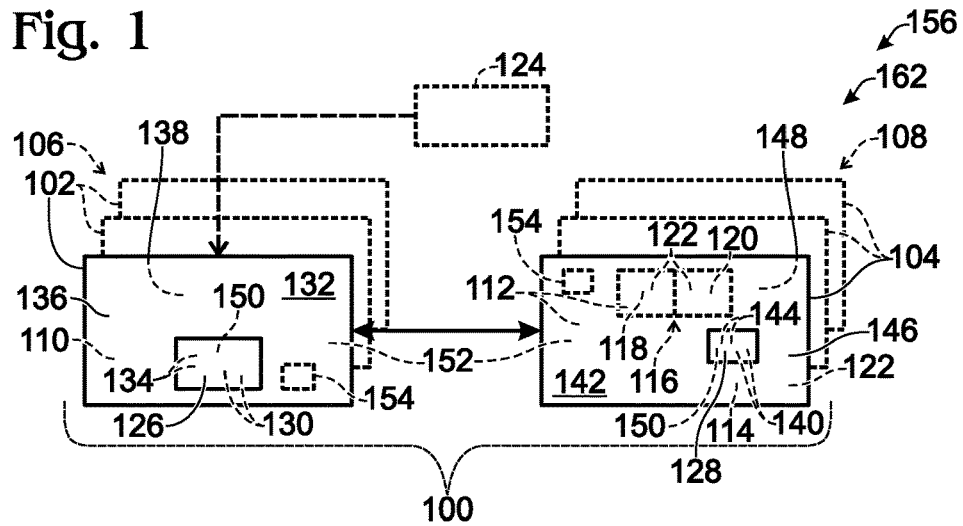
FIG. 1 is a schematic diagram of illustrative, non-exclusive examples of multi-part skin care bars according to the present disclosure.

FIG. 1 schematically illustrates examples of multi-part skin care bars 100 (which may also be referred to herein as bars 100) according to the present disclosure. Multi-part skin care bars 100 may be formed by coupling together a first portion 102 and a second portion 104. First portion 102 and second portion 104 may be configured to be coupled together, such as by having complementary features that are configured to engage with one another, as will be described in greater detail below. First portion 102 and second portion 104 may be formed of different materials having different properties from one another, such that a user using multi-part skin care bar 100 may experience different functions or results depending on how the bar is held (e.g., which side of the bar is being used on the skin). For example, first portion 102 may be configured to provide a cleansing and/or moisturizing effect, while second portion 104 may be configured to provide a cleansing, scrubbing, hair removal, massaging, and/or exfoliating effect. For example, first portion 102 may be composed of an emollient or moisturizing soap, and may include ingredients such as distilled water, glycerin, coconut oil, coconut acid, sodium carbonate, fragrance, sodium chloride, dye, lye (sodium hydroxide), avocado butter, almond oil, jojoba oil, tea tree oil, shea butter, olive oil, vegetable shortening, palm oil, soybean oil, vitamin E, and/or any other suitable ingredient. Second portion 104 may be composed of pumice, a pumice soap (e.g., soap including ground pumice), a different type of soap from that of first portion 102, and/or a plastic or other polymer, and may include ingredients such as fine or coarse ground pumice, bulk pumice, distilled water, glycerin, coconut acid, sodium carbonate, fragrance, sodium chloride, dye, lye, coconut oil, olive oil, palm oil, shea butter, tea tree oil, and/or any other suitable ingredient. The presently disclosed multi-part skin care bar may thus provide a user with both capabilities of exfoliation and also moisturizing in a single skin care bar. Fragrances also may be included in first portion 102 and/or second portion 104, such as by including ingredients such as lavender, aloe vera, hemp, rose petal, ginseng, oatmeal, pine, chocolate, patchouli, lemon, lime, basil, cinnamon, peppermint, cranberry, pomegranate, tea tree oil, chamomile, eucalyptus, menthol, honey, acai berry, sandalwood, fir, wood, leather, orange, vanilla, and/or any other synthetic or natural scent or ingredient.

In some examples, a plurality of first portions 106 may be provided, and/or a plurality of second portions 108 may be provided. In these examples, a respective first portion 102 may be selected from plurality of first portions 106, and a respective second portion 104 may be selected from plurality of second portions 108. Each respective first portion 102 may be used in place of each of the others of plurality of first portions 106, and each respective second portion 104 may be used in place of each of the others of plurality of second portions 108 (e.g., each respective first portion 102 of the plurality of first portions 106 may be configured to engage with any respective second portion 104 of the plurality of second portions 108). In this manner, multi-part skin care bars 100 may be customizable and/or interchangeable (e.g., users may "mix and match" respective first portions 102 and second portions 104), such that a variety of multi-part skin care bars 100 may be formed by selecting various first portions 102 from the plurality of first portions 106 and selecting various second portions 104 from the plurality of second portions 108. For example, a plurality 106 of first portions 102 may include a plurality of varieties of soap (e.g., having different ingredients, different colors, different scents, fragrance-free, and/or different degrees of moisturizing, etc.) and a plurality 108 of second portions 104 may include a plurality of varieties of pumice or pumice soaps (e.g., different strengths of pumice, different sizes of pumice particles, different types of pumice, different densities of pumice, different scents, different colors, etc.). Presently disclosed multi-part skin care bars 100 may be configured such that once a respective first portion 102 and second portion 104 are coupled together, they are generally difficult to separate. In some examples, once first portion 102 and second portion 104 are coupled together and used (e.g., wetted), they may be difficult or impossible to separate from one another without damaging either or both portions. In yet other examples, first portion 102 and second portion 104 may be selectively coupled together and separated.

In some examples, each first portion 102 of plurality of first portions 106 may have a substantially identical size and shape to each other respective first portion 102, thereby making each first portion 102 able to be used in place of each other first portion 102 of plurality of first portions 106 (e.g., each respective first portion 102 may be substitutable for any of the other first portions 102). Similarly, each second portion 104 of plurality of second portions 108 may have a substantially identical size and shape to each other respective second portion 104, thereby making each second portion 104 able to be used in place of each other second portion 104 of plurality of second portions 108 (e.g., each respective second portion 104 may be substitutable for any of the other second portions 104). Thus, any of the first portions 102 may be compatible with any of the second portions 104. In some examples, each first portion 102 may have a first size and/or shape, and each second portion 104 may have a second size and/or shape, the first size and/or first shape being different from the second size and/or second shape. For example, each first portion 102 may have a different yet complementary size and shape to each second portion 104. In other examples, each first portion 102 may have a substantially identical size and shape to each second portion 104.

First portion 102 and second portion 104 may be formed of different materials in order to form a multi-part skin care bar 100 having dual properties (e.g., different properties on either side of the bar). For example, first portion 102 may be formed of a soap 110 (e.g., an emollient or moisturizing soap), while second portion 104 may be formed of a scrubbing or exfoliating material 112, such as pumice 114 (e.g., pumice soap). In other examples, second portion 104 may be formed of a different scrubbing or exfoliating material 112, such as a polymer 122, such as in examples that include a plastic second portion 104. In some examples, second portion 104 may be a molded plastic part, a solid plastic part, and/or a hollow plastic part. In some examples, second portion 104 may include or be an elongate scrubber 116, such elongate scrubber 116 having a receiving portion 118 configured to engage with a respective first portion 102 and an elongate handle 120 extending therefrom. For example, elongate handle 120 may be configured such that a user may hold onto elongate handle 120 and be able to scrub or wash a hard-to-reach area (such as the user's back) with first portion 102 and/or second portion 104.

Some multi-part skin care bars 100 may include a cover element 124 that may be configured to cover some or all of first portion 102 and/or second portion 104. For example, in multi-part skin care bars 100 having a first portion 102 formed of soap, cover element 124 may be configured to cover first portion 102, such as to protect first portion 102 from damage or to protect other items from getting soap thereon (e.g., in instances were multi-part skin care bar 100 is traveled with and/or stored with other items). Cover element 124 may be configured to engage with second portion 104. For example, cover element 124 may be configured to snap onto second portion 104, thereby enclosing first portion 102 between cover element 124 and second portion 102.

First portion 102 may include a first engagement portion 126, and second portion 104 may include a second engagement portion 128, wherein first engagement portion 126 is configured to engage with second engagement portion 128 in order to couple first portion 102 to second portion 104 to form multi-part skin care bar 100. For example, first engagement portion 126 and second engagement portion 128 may be complementary halves of one or more of a mortise and tenon joint, a rabbit joint, a miter joint, a biscuit joint, a dovetail joint, a tongue and groove joint, and a dowel joint. In some bars 100, first engagement portion 126 and/or second engagement portion 128 may include one or more projections and/or one or more complementary pockets, or receiving holes, such that a respective projection may be inserted into a respective receiving hole to mate first engagement portion 126 and second engagement portion 128, thereby coupling first portion 102 to second portion 104. First engagement portion 126 and second engagement portion 128 may be configured to snap together, thereby coupling first portion 102 to second portion 104. In some examples, first portion 102 and second portion 104 may be snapped together, pressed together, or otherwise coupled together such that the joint between the engagement portions is sufficient to hold together first portion 102 and second portion 104 when only one side of the bar is being held. In other examples, once the portions have been initially coupled together, bar 100 may be wetted to enhance the joint between first portion 102 and second portions 104 (e.g., wetting the bar may increase the ability of the portions to stick together, and/or may cause the portions to fuse together in some examples). Additionally or alternatively, first portion 102 and/or second portion 104 may be wetted before coupling together to form bar 100.

In some examples, first engagement portion 126 may include a first projection 130 extending from a first surface 132 of first portion 102. In some examples, first projection 130 may be a plurality of first projections 130. First projection 130 may include, for example, a cylindrical dowel, a peg, a square projection, or any other three-dimensional shape that may extend from first surface 132 of first portion 102. First projection 130 may be formed integrally with first portion 102 (e.g., formed of the same material as first portion 102), or first projection 130 may be formed of a different material or materials from first portion 102 in some examples. First projection 130 may extend a minimum distance from first surface 132. For example, first projection 130 may extend at least 2.5 mm, at least 5 mm, at least 7.5 mm, at least 10 mm, at least 15 mm, at least 20 mm, at least 25 mm, and/or greater than 25 mm from first surface 132. In some examples, the length of first projection 130 may be at least 25% of the thickness of first portion 102, at least 50% of the thickness of first portion 102, at least 75% of the thickness of first portion 102, and/or equal to or greater than the thickness of first portion 102.

Additionally or alternatively, first engagement portion 126 may include a first receiving hole 134. First receiving hole 134 may extend from first surface 132 into the thickness of first portion 102 (e.g., into a body 136 of first portion 102) and towards a second surface 138 (second surface 138 being opposite first surface 132). In some examples, first receiving hole 134 may include two or more first receiving holes 134. First receiving hole 134 may extend a minimum distance from first surface 132 into body 136 of first portion 102. For example, first receiving hole 134 may have a depth of at least 2.5 mm, at least 5 mm, at least 7.5 mm, at least 10 mm, at least 15 mm, at least 20 mm, at least 25 mm, and/or greater than 25 mm from first surface 132 into body 136. In some examples, the depth of first receiving hole 134 may be at least 25% of the thickness of first portion 102, at least 50% of the thickness of first portion 102, and/or at least 75% of the thickness of first portion 102. In some examples, first engagement portion 126 may include one or more first projections 130 and one or more first receiving holes 134. For example, first engagement portion 126 may include one first projection 130 and one first receiving hole 134. In other examples, first engagement portion 126 may include two first projections 130 and no first receiving hole 134. Alternatively, first engagement portion 126 may include a plurality of first projections 130 and/or a plurality of first receiving holes 134.

Similarly, second engagement portion 128 may include a second projection 140 extending from a first surface 142 of second portion 104. In some examples, second projection 140 may be a plurality of second projections 140. Second projection 140 may include, for example, a cylindrical dowel, a peg, a square projection, or any other three-dimensional shape that may extend from first surface 142 of second portion 104. Second projection 140 may be formed integrally with second portion 104 (e.g., formed of the same material as second portion 104), or second projection 140 may be formed of a different material or materials from second portion 104 in some examples. Second projection 140 may extend a minimum distance from first surface 142. For example, second projection 140 may extend at least 2.5 mm, at least 5 mm, at least 7.5 mm, at least 10 mm, at least 15 mm, at least 20 mm, at least 25 mm, and/or greater than 25 mm from first surface 142. In some examples, the length of second projection 140 may be at least 25% of the thickness of second portion 104, at least 50% of the thickness of second portion 104, at least 75% of the thickness of second portion 104, and/or equal to or greater than the thickness of second portion 104.

Additionally or alternatively, second engagement portion 128 may include a second receiving hole 144. Second receiving hole 144 may extend from first surface 142 into the thickness of second portion 104 (e.g., into a body 146 of second portion 104) and towards a second surface 148 (second surface 148 being opposite first surface 142). In some examples, second receiving hole 144 may include two or more second receiving holes 144. Second receiving hole 144 may extend a minimum distance from first surface 142 into body 146 of second portion 104. For example second receiving hole 144 may have a depth of at least 2.5 mm, at least 5 mm, at least 7.5 mm, at least 10 mm, at least 15 mm, at least 20 mm, at least 25 mm, and/or greater than 25 mm from first surface 142 into body 146. In some examples, the depth of second receiving hole 144 may be at least 25% of the thickness of first portion 102, at least 50% of the thickness of first portion 102, and/or at least 75% of the thickness of second portion 104. In some examples, second engagement portion 128 may include one or more second projections 140 and one or more second receiving holes 144. For example, second engagement portion 128 may include one second projection 140 and one second receiving hole 144. In other examples, second engagement portion 128 may include two second projections 140 and no second receiving hole 144. Alternatively, second engagement portion 128 may include a plurality of second projections 140 and/or a plurality of second receiving holes 144.

In some examples, first engagement portion 126 and second engagement portion 128 may be configured to be complementary, such that first engagement portion 126 and second engagement portion 128 may be configured to engage with one another in order to couple first portion 102 to second portion 104, thereby forming multi-part skin care bar 100. For example, first projection 130 of first engagement portion 126 may be configured to be inserted into second receiving hole 144 of second engagement portion 128, and second projection 140 of second engagement portion 128 may be configured to be inserted into first receiving hole 134 of first engagement portion 126. The projections may be configured to have a friction fit within the receiving holes in some examples. For example, the diameter of first projection 130 may be approximately equal to, or slightly greater than, the diameter of second receiving hole 144. Similarly, the diameter of second projection 140 may be approximately equal to, or slightly greater than, the diameter of first receiving hole 134. Additionally or alternatively, first projection 130 and/or second projection 140 may be configured to fuse to the interior of second receiving hole 144 and/or first receiving hole 134, respectively. In some examples, the diameter of first receiving hole 134 and/or second receiving hole 144 may change along the depth of the hole. For example, the diameter or first receiving hole 134 and/or second receiving hole 144 may become larger or smaller along the length of the hole, from first surface 132, 142, respectively, towards second surface 138, 148, respectively (e.g., first receiving hole 134 and/or second receiving hole 144 may be slightly cone-shaped in some examples).

Multi-part skin care bar 100, when assembled, may take the shape and size of a conventional skin care bar in some examples. For example, multi-part skin care bar 100 may be sized and shaped to fit comfortably within a user's hand in some examples. In some examples, the assembled multi-part skin care bar 100 may be approximately a rectangular prism in shape, with rounded corners and edges, although other shapes are also possible. For example, assembled multi-part skin care bar 100 may be approximately spherical, with first portion 102 and second portion 104 each being approximately hemispherical. In some examples, second surface 138 of first portion 102 and/or second surface 148 of second portion 104 may be substantially smooth and/or flat and/or may be embossed or engraved with a logo or design. Second surface 138 of first portion 102 and second surface 148 of second portion 104 may be facing out, forming the outer surfaces of assembled multi-part skin care bar 100.

First surface 132 of first portion 102 may be positioned adjacent and facing first surface 142 of second portion 104 when first portion 102 and second portion 104 are coupled together to form multi-part skin care bar 100 (e.g., first surface 132 of first portion 102 and first surface 142 of second portion 104 may be arranged to be engaged with one another and internal, due to first engagement portion 126 and second engagement portion 128 being positioned on first surface 132 of first portion 102 and first surface 142 of second portion 104, respectively). First surface 132 of first portion 102 and/or first surface 142 of second portion 104 may be substantially flat in some examples. In some examples, first surface 132 of first portion 102 and/or first surface 142 of second portion 104 may be substantially flat except in the areas of first engagement portion 126 and second engagement portion 128, respectively. In other examples, first surface 132 of first portion 102 and/or first surface 142 of second portion 104 may be curved, contoured, wavy, textured, and/or have any other three-dimensional shape. For example, first surface 132 of first portion 102 and first surface 142 of second portion 104 may each have a complementary S-shaped surface, such that when first portion 102 and second portion 104 are coupled together, first surface 132 of first portion 102 and first surface 142 of second portion 104 form a smooth interface therebetween.

In some examples, the inner surfaces of first portion 102 and/or second portion 104 (e.g., first surface 132 of first portion 102 and/or first surface 142 of second portion 104) may include a plurality of gripping features 150 extending therefrom or positioned thereon (e.g., first engagement portion 126 and/or second engagement portion 128 may include a plurality of gripping features 150 configured to engage the other respective portion). For example, first surface 132 of first portion 102 may include a plurality of gripping features 150 extending therefrom and configured to engage (e.g., be forced into or stick to) first surface 142 of second portion 104. Additionally or alternatively, first surface 142 of second portion 104 may include a plurality of gripping features 150 extending therefrom or positioned thereon and configured to engage first surface 132 of first portion 102. Once first portion 102 and second portion 104 have been coupled together to form multi-part skin care bar 100, any plurality of gripping features 150 present on first surface 132 of first portion 102 and/or first surface 142 of second portion 104 may be sandwiched between first portion 102 and second portion 104 such that the plurality of gripping features 150 are not visible when the multi-part skin care bar 100 is assembled. In some examples, when first portion 102 and second portion 104 are coupled together, the plurality of gripping features 150 of one of the portions may be at least partially embedded within the other portion. For example, the plurality of gripping features 150 of first portion 102 may be configured to puncture, pierce, or otherwise cut into second portion 104, and/or the plurality of gripping features 150 of second portion 104 may be configured to puncture, pierce, or otherwise cut into first portion 102. In some examples, both first portion 102 and second portion 104 may include a plurality of gripping features 150. In other examples, just one of first portion 102 and second portion 104 may include a plurality of gripping features 150. In yet other examples, neither first portion 102 nor second portion 104 may include a plurality of gripping features 150 on one of the surfaces. Gripping features 150 may include, for example, teeth, barbs, grooves, notches, tapered projections, pointed projections, and/or any other features that may be configured to increase friction between first portion 102 and second portion 104 and/or configured to increase the surface area for coupling first portion 102 to second portion 104.

In some examples, the outer surfaces of first portion 102 and/or second portion 104 (e.g., second surface 138 of first portion 102 and/or second surface 148 of second portion 104) may include a plurality of scrubber bristles 152 extending therefrom. Scrubber bristles 152 may be, for example, a series of small plastic or rubber scrubber projections, arranged in a plurality of parallel rows or columns. Scrubber bristles 152 may be configured to be used on a user's skin to massage, exfoliate, and/or cleanse. Scrubber bristles 152 may be formed integrally with (e.g., integrally molded with) first portion 102 and/or second portion 104 in some examples.

Some multi-part skin care bars 100 may include a notched hole 154, which may extend all the way through the body of the portion (e.g., all the way through body 136 of first portion 102 or all the way through body 146 of second portion 104). In other words, notched hole 154 may extend from first surface 132 to second surface 138 of first portion 102, or from first surface 142 to second surface 148 of second portion 104. Notched hole 154 may include one or more notches formed in the interior of notched hole 154. In some examples, notched hole 154 may be star-shaped, formed with a zig-zag pattern formed into a circular shape. Notched hole 154 may be part of first engagement portion 126 and/or second engagement portion 128. For example, in a multi-part skin care bar 100 having a first portion 102 formed of soap and a second portion 104 formed of plastic, second portion 104 may include a notched hole 154 extending therethrough, and at least a portion of first engagement portion 126 of first portion 102 may be configured to be inserted into notched hole 154. First engagement portion 126 may engage with the notches of notched hole 154 such that notched hole 154 grips onto first engagement portion 126 (e.g., notched hole 154 may grip onto a first projection 130 of first engagement portion 126 that is inserted into notched hole 154). In some examples, notched hole 154 may provide an access point for separating first portion 102 and second portion 104. For example, a user may be able to insert a finger or a small tool through notched hole 154 formed in second portion 104, in order to push first portion 102 off of second portion 104. For example, in a multi-part skin care bar 100 having a second portion 104 formed of plastic, first portion 102 may be removable from second portion 104 when a user wishes to switch to a different variety of first portion 102, or when first portion 102 is worn away enough that a user desires to remove it and reuse second portion 104 with a different first portion 102. Additionally or alternatively, notched hole 154 may be an example of second receiving hole 144.

FIG. 1 also illustrates a system 156 that includes a plurality 106 of first portions 102 each having a respective first engagement portion 126 and a plurality 108 of second portions 104 each having a respective second engagement portion 128. Each of the plurality 108 of second portions 104 may be configured to be coupled to a respective one of the plurality 106 of first portions 102 via the respective first engagement portion 126 and respective second engagement portion 128 to form multi-part skin care bar 100.

Turning now to FIGS. 2-15, illustrative non-exclusive examples of multi-part skin care bars and portions thereof are illustrated. Where appropriate, the reference numerals from the schematic illustration of FIG. 1 are used to designate corresponding parts in FIGS. 2-15; however, the examples of FIGS. 2-15 are non-exclusive and do not limit multi-part skin care bars to the illustrated embodiments. That is, multi-part skin care bars are not limited to the specific embodiments of the illustrated FIGS. 2-15, and may incorporate any number of the various aspects, configurations, characteristics, properties, etc. of multi-part skin care bars that are illustrated in and discussed with reference to the schematic representation of FIG. 1 and/or the embodiments of FIGS. 2-15, as well as variations thereof, without requiring the inclusion of all such aspects, configurations, characteristics, properties, etc. For the purpose of brevity, each previously discussed component, part, portion, aspect, region, etc. or variants thereof may not be discussed, illustrated, and/or labeled again; however, it is within the scope of the present disclosure that the previously discussed features, variants, etc. may be utilized with each embodiment.

Figure 2:
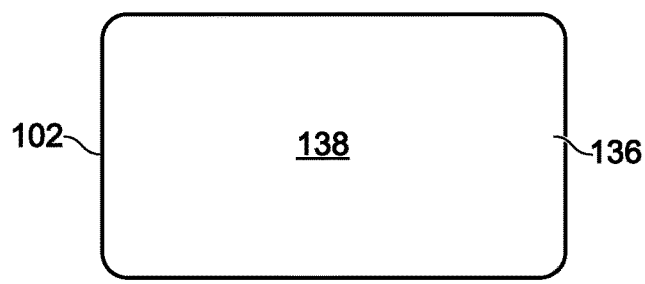
FIG. 2 is a top plan view of one example of a portion of a multi-part skin care bar according to the present disclosure.

FIGS. 2-6 illustrate a first embodiment of multi-part skin care bar 100 (FIGS. 5-6) having first portion 102 (FIGS. 2-3 and 5-6) and second portion 104 (FIGS. 4-6) that are coupled together to form multi-part skin care bar 100. FIG. 2 shows a top plan view of first portion 102, with second surface 138 of first portion 102 visible. FIG. 2 shows second surface 138 of first portion 102 having a rectangular shape with rounded corners; however, any other shape also is within the scope of the present disclosure. Second surface 148 of second portion 104 (seen in FIGS. 5-6) may appear identical to second surface 138 of first portion 102. Second surface 138 of first portion 102 and/or second surface 148 of second portion 104 may be substantially smooth or flat in some examples. For example, in multi-part skin care bars 100 where second portion 104 is formed of bulk pumice, second surface 148 of second portion 104 may be substantially flat in that the general form of the pumice is smooth or flat, despite pores or holes that may exist in the pumice.

FIG. 3 shows a bottom plan view of first surface 132 of first portion 102. The example of FIG. 3 shows first portion 102 having first engagement portion 126 that includes two first projections 130 extending from first surface 132 of first portion 102. First projections 130 may be substantially cylindrical, dowel-like projections in some examples, but other shapes are also possible. FIG. 4 shows a top plan view of first surface 142 of second portion 104. The example of FIG. 4 shows second portion 104 having second engagement portion 128 that includes two second receiving holes 144 extending from first surface 142 of second portion 104 and into body 146 of second portion 104. Second receiving holes 144 may be substantially circular in cross-sectional shape and may extend through a portion of the thickness of body 146 of second portion 104; however other shapes are also possible.

Figure 5:
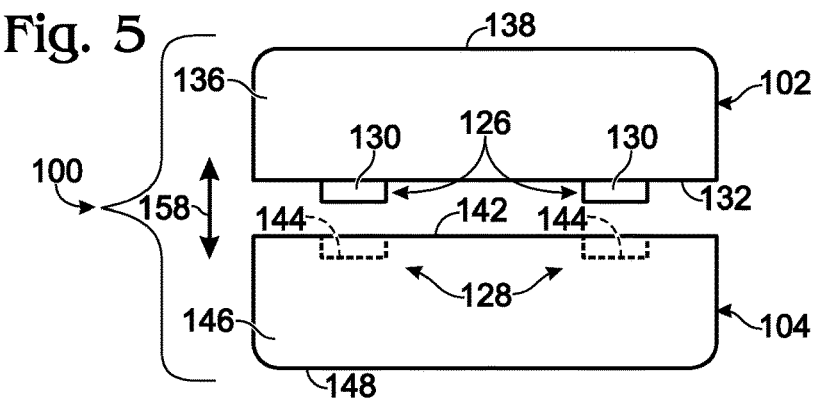
FIG. 5 is a side elevation view of a first portion and a second portion of a multi-part skin care bar according to the present disclosure.
Figure 6:
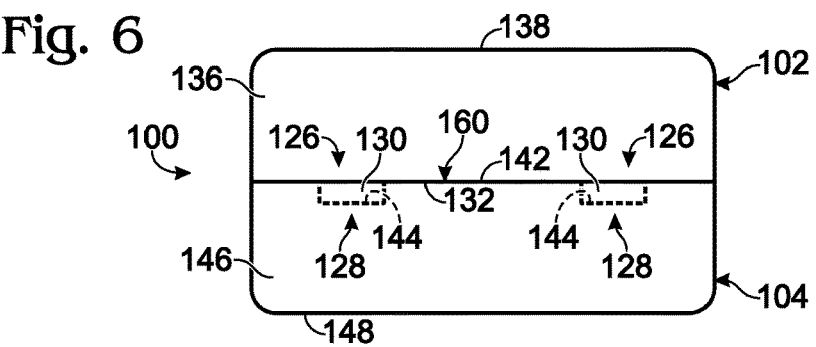
FIG. 6 is a side elevation view of the first portion and second portion shown in FIG. 5, shown coupled together according to the present disclosure.

As shown in FIG. 4, second engagement portion 128 (e.g., second receiving holes 144) may be sized, shaped, and positioned to be complementary to first engagement portion 126. For example, as shown in the side elevation views of FIGS. 5 and 6, first projections 130 of first portion 102 may be inserted into second receiving holes 144 of second portion 104 in order to couple first portion 102 to second portion 104, thereby forming multi-part skin care bar 100. As seen in FIG. 5, first portion 102 and second portion 104 may be aligned with one another such that first engagement portion 126 and second engagement portion 128 are aligned with one another. First portion 102 and second portion 104 may then be moved towards each other (such as by moving first portion 102 and/or second portion 104 in the directions indicated by arrow 158) and pressed together until the engagement portions are fully engaged with one another. As shown in FIG. 6, when first portion 102 and second portion 104 are coupled together, first surface 132 of first portion 102 and first surface 142 of second portion 104 may be in contact, flush with one another, and/or engaged with one another such that a substantially smooth interface 160 is formed therebetween. In some examples, such as when first portion 102 comprises soap and second portion 104 includes pumice (e.g., bulk pumice), interface 160 may be considered to be substantially "flat" or "smooth" despite any surface irregularities due to porosity of the pumice (e.g., in the case of bulk pumice). As seen in FIGS. 5-6, first surface 132 of first portion 102 and first surface 142 of second portion 104 may be substantially flat, e.g., substantially flat, planar, or parallel with the respective opposite second surface, except in the areas of first engagement portion 126 and second engagement portion 128, respectively (e.g., first surface 132 of first portion 102 may be substantially flat or planar, except where first projections 130 extend therefrom).

FIGS. 7-9 illustrate side elevation views of a second embodiment of multi-part skin care bar 100, shown assembled in FIG. 9. FIG. 7 illustrates first portion 102 and FIG. 8 illustrates second portion 104, which may be coupled together to form multi-part skin care bar 100. First engagement portion 126 may include first projection 130 and a first receiving hole 134, and second engagement portion 128 may include a second projection 140 and second receiving hole 144. The engagement portions 126, 128 may be configured to be complementary and engage with one another, such that first projection 130 may be inserted into second receiving hole 144 and/or second projection 140 may be inserted into first receiving hole 134, as shown in FIG. 9. In some examples, first portion 102 may include first receiving hole 134 even if it is not used (e.g., one or more first receiving holes 134 may not receive a respective second projection 140). Similarly, in some examples, second portion 104 may include second receiving hole 144 even if it is not used (e.g., one or more second receiving holes 144 may not receive a respective first projection 130).

Also as illustrated, first surface 132 of first portion 102 and first surface 142 of second portion 104 may be contoured, having a wavy, three-dimensional S-like shape. First surface 132 of first portion 102 and first surface 142 of second portion 104 may be complementary such that when first portion 102 is coupled to second portion 104, a substantially flat or smooth interface 160 may be formed therebetween, as shown in FIG. 9. It may be noted that first portion 102 and second portion 104 may be substantially identical in shape (e.g., if second portion 104 of FIG. 8 is rotated 180 degrees, it may appear substantially identical in shape to first portion 102 of FIG. 7). In this manner, first portion 102 may be used in place of any of a plurality of other first portions 102 and second portion 104 may be used in place of any of a plurality of other second portions 104, such that any selected first portion 102 may be coupled with any selected second portion 104 to customize multi-part skin care bar 100. Additionally or alternatively, any two respective first portions 102 may be coupled together to customize multi-part skin care bar 100 and/or any two respective second portions 104 may be coupled together to customize multi-part skin care bar 100.

FIGS. 10-12 illustrate another embodiment of portions that may be coupled together to form a multi-part skin care bar 100 according to the present disclosure. FIGS. 10-11 show side elevations of first portion 102 (FIG. 10) and second portion 104 (FIG. 11), and FIG. 12 shows a bottom plan view of second portion 104. The example of FIGS. 10-12 shows first portion 102 having first engagement portion 126 that includes a single first projection 130 extending from first surface 132 of first portion 102. First surface 132 of first portion 102 is also shown having a three-dimensional contoured shape, and may be substantially S-shaped, except where first projection 130 extends therefrom. First portion 102 may optionally include one or more first receiving holes 134, even in examples where second portion 104 does not include one or more second projections 140 to engage first receiving holes 134. In some examples, first portion 102 of FIG. 10 may be identical in size and shape to the embodiment shown in FIG. 7. In some examples, first portion 102 of FIG. 10 may not include any first receiving holes 134 and/or may have a longer first projection 130 than shown in the example of FIG. 7. In other examples, first projection 130 may be approximately equal in length in the examples of FIG. 7 and FIG. 10.

Second portion 104 (FIG. 11) may include a plurality of teeth 150 extending outward from first surface 142 of second portion 104. Additionally or alternatively, second engagement portion 128 may include second receiving hole 144, which may be a notched hole 154 that extends all the way through body 146 of second portion 104, from first surface 142 of second portion 104 to second surface 148 of second portion 104. Notched hole 154 may be configured to receive first projection 130 of first portion (FIG. 10), and plurality of teeth 150 may be configured to engage first surface 132 of first portion 102, in order to couple first portion 102 to second portion 104. For example, second portion 104 may be formed of pumice, pumice soap, and/or a polymer, first portion 102 may be formed of soap, and teeth 150 may be configured to be embedded into the soap of first portion 102, thereby coupling first portion 102 to second portion 104. First projection 130 may be configured to extend at least a portion of the way through notched hole 154, such that soap may be available to the user when the user is using second portion 104 (e.g., when the user is holding multi-part skin care bar 100 such that second portion 104, which may be composed of something other than soap, is in contact with the user's skin). In some examples, notched hole 154 may enable a user to push first portion 102 off of second portion 104 by pushing on first projection 130 through notched hole 154, thereby allowing reuse of second portion 104 with a different respective first portion 102.

Additionally or alternatively, second portion 104 may include a plurality of scrubber attachments 152 extending from second surface 148 of second portion 104. Such scrubber attachments 152 may be configured to be facing outward when the multi-part skin care bar is assembled, and as shown in FIG. 12, may be arranged in any suitable fashion, such as in a series of parallel rows or columns. Any number of scrubber attachments 152 may be included, and the example shown is for illustrative purposes only. Scrubber attachments 152 may be formed of, for example, a semi-flexible polymer or rubber, and may be configured to be used directly on a user's skin, to enhance use of the multi-part skin care bar.

FIG. 13 illustrates a side elevation view of a cover element 124 that may be used with multi-part skin care bars 100 according to the present disclosure. Cover element 124 may be, for example, formed of a polymer or any other suitable material, and may be configured to be selectively coupled to first portion 102 and/or second portion 104 of a multi-part skin care bar 100. Cover element 124 may be approximately the same shape as first portion 102 and/or second portion 104, but may be slightly larger than first portion 102 and/or second portion 104 such that cover element 124 may be placed over first portion 102 and/or second portion 104, thereby enclosing first portion 102 and/or second portion 104. For example, in a multi-part skin care bar 100 having a first portion 102 composed of soap, and a second portion 104 composed of plastic, a cover element 124 may be used to cover first portion 102, thereby preventing soap from getting on other items when not in use. In this example, cover element 124 may have a snap fit with second portion 104 in order to selectively place and remove cover element 124, but any other arrangement is also possible. Cover element 124 may generally be formed of a thin hollow shell 164 that defines a cavity 166, the cavity 166 being sized and shaped to receive a respective first portion 102 or second portion 104 such that cover element 124 may enclose first portion 102 between cover element 124 and second portion 104.

FIGS. 14-15 illustrate another embodiment of multi-part skin care bar 100, which includes a second portion 104 having an elongate handle 120. FIG. 14 shows a side elevation view of the multi-part skin care bar, and FIG. 15 shows a bottom plan view of the same. The example of FIGS. 14-15 includes a first portion 102 having a first projection 130 that is inserted through a notched hole 154 formed in second portion 104. Second portion 104 also includes a plurality of teeth 150 that are configured to engage first surface 132 of first portion 102, and a plurality of scrubber attachments 152 extending from second surface 148 of second portion 104. Elongate handle 120 may extend from a receiving portion 118 (e.g., first surface 142 of second portion 104), and a scrubbing portion 116 may be positioned on second surface 148 of second portion 104. Elongate handle 120 may be configured to allow a user to scrub or clean a hard-to-reach location, such as the user's back.

While examples illustrate a two-part multi-part skin care bar 100, other configurations are also possible. For example, multi-part skin care bars 100 may include three or four or more portions coupled together, such as arranged as a stack of layers, or arranged in some other fashion. Furthermore, multi-part skin care bars 100 may be sold as part of a kit 162 (FIG. 1), which may include one or more first portions 102, one or more second portions 104, and/or one or more cover elements 124. For example, a kit 162 may include a plurality of first portions 102, a plurality of second portions 104, and a cover element 124. One example of kit 162 may include an assortment of between 6 and 10 different first portions 102 and/or an assortment of between 6 and 10 different second portions 104. Another example of a kit 162 may include a plurality of second portions 104, where at least one second portion 104 includes an elongate handle 120, and at least one of the second portions 104 has no handle.

Figure 16:
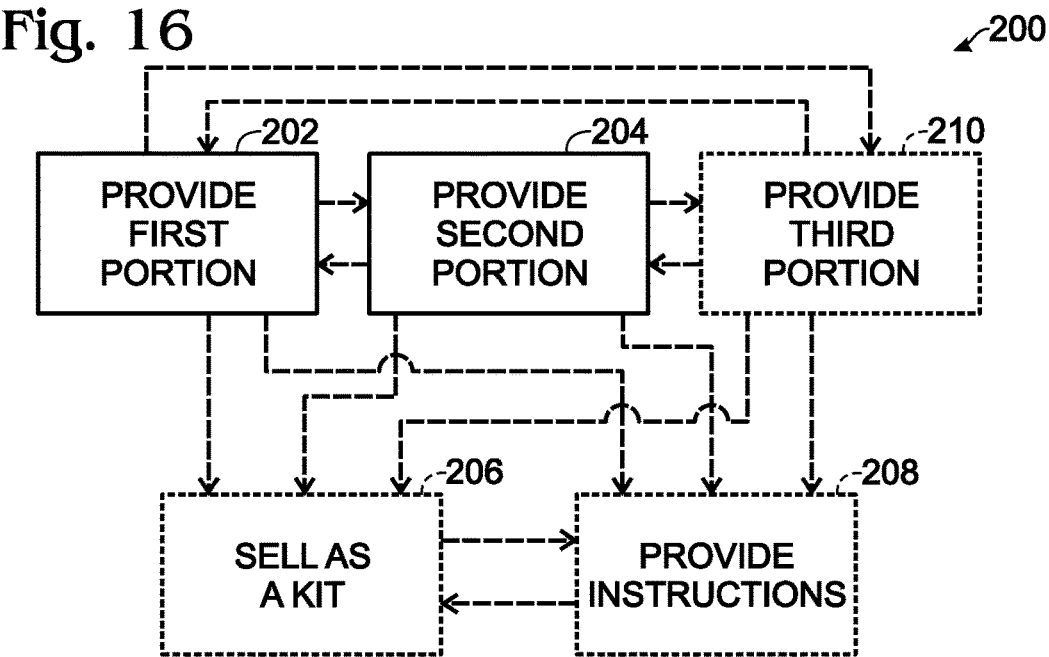
FIG. 16 is a schematic flow chart diagram illustrating methods according to the present disclosure.
Figure 17:
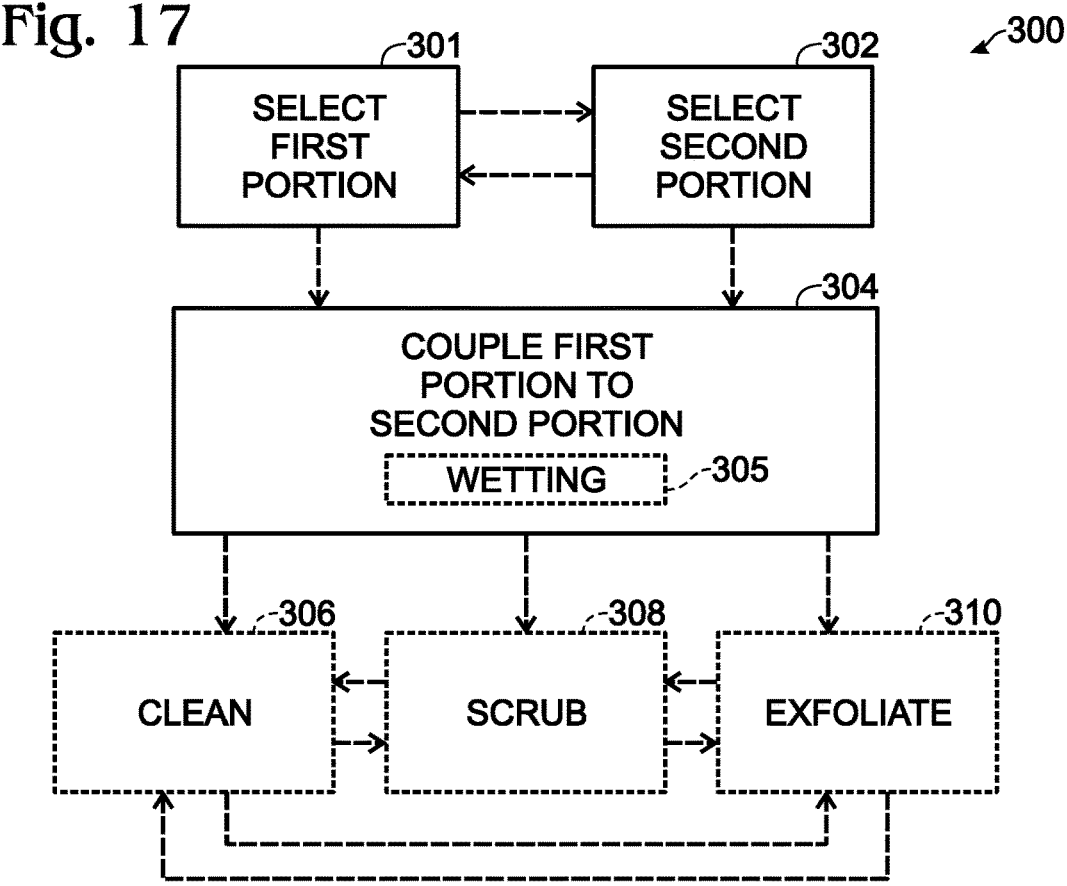
FIG. 17 is a schematic flow chart diagram illustrating methods of using a multi-part skin care bar according to the present disclosure.

FIGS. 16-17 schematically provide flowcharts that represent illustrative, non-exclusive examples of methods according to the present disclosure. In FIGS. 16-17, some steps are illustrated in dashed boxes indicating that such steps may be optional or may correspond to an optional version of a method according to the present disclosure. That said, not all methods according to the present disclosure are required to include the steps illustrated in solid boxes. The methods and steps illustrated in FIGS. 16-17 are not limiting and other methods and steps are within the scope of the present disclosure, including methods having greater than or fewer than the number of steps illustrated, as understood from the discussions herein.

FIG. 16 illustrates methods 200 of providing a multi-part skin care bar (e.g., multi-part skin care bar 100) according to the present disclosure. Methods 200 may include providing a first portion of a multi-part skin care bar (e.g., first portion 102) at 202. The first portion may be composed of a first material, such as soap. In some examples, providing a first portion at 202 may include providing a plurality of first portions, each of which may be composed of the same material, or which may include a plurality of different materials in different respective first portions. For example, some of the plurality of first portions may be a first variant (e.g., a soap having a first scent), and others of the plurality of first portions may be a second variant (e.g., a soap having a second scent different from the first scent). In other examples, different variants among the plurality of first portions may include different soaps, or different soap ingredients, and/or different levels of moisturizer in the different variants. A user may select any of the variants of the plurality of first portions.

Methods 200 also may include providing a second portion of a multi-part skin care bar (e.g., second portion 104) at 204. The second portion may be composed of a second material, which, in some methods, may be different from the first material (e.g., the second material may include pumice, pumice soap, and/or plastic). In some examples, providing a second portion at 204 may include providing a plurality of second portions, each of which may be identical in some examples, or the plurality of second portions may include a variety of different second portions (e.g., an assortment of different pumice strengths may be included in the plurality of second portions, or some of the plurality of second portions may be formed of plastic while others of the plurality of second portions may be formed of pumice or pumice soap). In some methods, the plurality of second portions may include one or more second portions of a first variety and one or more second portions of a second variety. For example, some of the plurality of second portions may be formed of pumice or pumice soap, some of the plurality of second portions may be formed of plastic, and/or some of the plurality of second portions may include an elongate handle and/or scrubber portion.

Each respective first portion may be configured to have a complementary shape to each respective second portion such that each respective first portion is configured to engage with any respective second portion to form the multi-part skin care bar according to the present disclosure. Thus, the providing the plurality of first portions at 202 and the providing the plurality of second portions at 204 may enable providing a plurality of interchangeable and/or customizable, multi-part skin care bars according to the present disclosure.

Providing the first portion at 202 may include selling the first portions individually and/or selling the first portions as a bundle or part of a kit (e.g., kit 162) at 206. Similarly, providing the second portion at 204 may include selling the second portions individually and/or selling the second portions as a bundle or part of a kit at 206. Additionally or alternatively, methods 200 may include providing instructions regarding the multi-part skin care bar at 208. For example, providing instructions at 208 may include displaying information instructing a user to engage and/or couple a respective first portion together with a respective second portion to form the multi-part skin care bar. Providing instructions at 208 may include providing written instructions, verbal instructions, and/or illustrated instructions. Providing instructions at 208 may include providing specific instructions as to how to couple the first portion to the second portion, such as providing instructions to insert a first projection (e.g., first projection 130) of a respective first portion into a second receiving hole (e.g., second receiving hole 144) of a second portion. Additionally or alternatively, providing instructions at 208 may include providing instructions to insert a second projection (e.g., second projection 140) of a respective second portion into a first receiving hole (e.g., first receiving hole 134) of a respective first portion.

Methods 200 may include providing a third portion (e.g., a cover element 124) at 210, or a plurality of third portions, which may be useable with the first portion and second portion. For example, providing a third portion at 210 may include providing a cover element that may be used to engage with the second portion and cover the first portion when the first portion and second portion are coupled together. Generally, the first portion and second portion may be configured such that they are intended to remain coupled once engaged with one another, and the third portion may be configured to be selectively removable from the assembled multi-part skin care bar.

In some methods 200, selling the portions as a kit at 206 may include selling a kit comprising one or more first portions and one or more second portions, each respective first portion being configured to be coupled to a respective second portion via complementary features formed on and/or in the first portion and the second portion (e.g., via first engagement portion 126 and second engagement portion 128), wherein coupling a respective first portion to a respective second portion forms a multi-part skin care bar. In some methods, the second portion may be configured to be reusable with a plurality of different first portions. For example, in multi-part skin care bars having a plastic second portion, a kit may be sold at 206 where the kit includes a single second portion and a plurality or assortment of different first portions, such that a user may select one first portion to be used with the second portion, and then the user may select another respective first portion to be used with the same second portion once the initial first portion is gone (e.g., once the soap is used up) or the user otherwise desires to switch to a different first portion.

FIG. 17 illustrates methods 300 of using a multi-part skin care bar according to the present disclosure. Methods 300 may include selecting a first portion (e.g., first portion 102) at 301, such as selecting a respective first portion from a plurality of first portions. Methods 300 may include selecting a second portion (e.g., second portion 104) at 302, such as selecting a respective second portion from a plurality of second portions. Once the first portion and second portion have been selected, they may be coupled together to form a multi-part skin care bar (e.g., multi-part skin care bar 100) at 304. Forming the multi-part skin care bar at 304 may include engaging a first engagement portion (e.g., first engagement portion 126) and a second engagement portion (e.g., second engagement portion 128) in order to couple the first portion to the second portion. For example, coupling the portions at 304 may include pressing the first portion and second portion together, embedding teeth from one portion into another, and/or inserting a projection from one or both portions into a respective receiving hole in the other portion. In some examples, coupling the first portion to the second portion at 304 may include wetting the multi-part skin care bar at 305, which may cause the portions to stick and/or fuse together in some methods.

Thus formed, the multi-part skin care bar may be used by a user, such as by cleaning a portion of the user's body at 306, scrubbing a portion of the user's body at 308, and/or exfoliating a portion of the user's body at 310. For example, cleaning a portion of the user's body at 306 may include using the side of the multi-part skin care bar corresponding to the first portion to clean the user's body. Scrubbing at 308 and/or exfoliating at 310 may include using the other side of the multi-part skin care bar, corresponding to the second portion, which may be formed of pumice or pumice soap and/or which may include a scrubbing portion. The multi-part skin care bar may be used multiple times without requiring reassembly or other maintenance between uses. The multi-part skin care bar may be sized and shaped to be handheld, such that a user may comfortably hold the bar in a single hand during use. The multi-part skin care bar also may be advantageously sized and/or shaped such that it may be used to clean small, rough areas of the body, such as elbows, legs, lower back, feet, buttocks, bearded areas, and/or any other area of the body. Multi-part skin care bars may be reused a plurality of times (e.g., only a small volume of soap contained within the bar may be used at each use), and stored between uses, such as in a shower, on a sink ledge, in a soap dish, on a bathtub ledge, or on a shelf or counter. In some examples, multi-part skin care bars may include up to 5 oz. (141 g) of soap, up to 10 oz. (283 g) of soap, up to 15 oz. (425 g) of soap, and/or 20 oz. (566 g) or more of soap. In one specific example, multi-part skin care bars may include about 11.5 oz. (326 g) of soap, which may provide a sufficient quantity of soap for a plurality of uses (e.g., at least 5 uses, at least 10 uses, at least 15 uses, at least 20 uses, at least 25 uses, and/or 30 or more uses).

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus.

Illustrative, non-exclusive examples of inventive subject matter according to the present disclosure are described in the following enumerated paragraphs:

A1. A multi-part skin care bar, comprising:
a first portion; and
a second portion, wherein the first portion and the second portion are configured to be coupled together to form the multi-part skin care bar.

A2. The multi-part skin care bar of paragraph A1, wherein the first portion comprises a plurality of first portions, the second portion comprises a plurality of second portions, and wherein each respective first portion of the plurality of first portions is configured to engage with any respective second portion of the plurality of second portions.

A3. The multi-part skin care bar of any of paragraphs A1-A2, wherein the first portion comprises a plurality of first portions, each of the plurality of first portions having an identical size and shape, and wherein the second portion comprises a plurality of second portions, each of the plurality of second portions having an identical size and shape.

A4. The multi-part skin care bar of paragraph A3, wherein each of the plurality of first portions and each of the plurality of second portions have an identical size and shape to each other.

A5. The multi-part skin care bar of any of paragraphs A1-A4, wherein the first portion comprises soap.

A6. The multi-part skin care bar of any of paragraphs A1-A5, wherein the second portion comprises pumice.

A7. The multi-part skin care bar of any of paragraphs A1-A5, wherein the second portion is constructed of plastic.

A8. The multi-part skin care bar of any of paragraphs A1-A7, wherein the second portion comprises an elongate scrubber, the elongate scrubber having an elongate handle extending from a receiving portion, the receiving portion being configured to engage with the first portion.

A9. The multi-part skin care bar of any of paragraphs A1-A8, further comprising a cover element configured to cover the first portion.

A10. The multi-part skin care bar of paragraph A9, wherein the cover element is configured to engage with the second portion.

A11. The multi-part skin care bar of paragraph A10, wherein the cover element is configured to have a snap fit engagement with the second portion, thereby enclosing the first portion between the cover element and the second portion.

A12. The multi-part skin care bar of any of paragraphs A1-A11, wherein the first portion comprises a first engagement portion and the second portion comprises a second engagement portion, wherein the first portion and the second portion are configured such that the first engagement portion is configured to engage with the second engagement portion in order to couple the first portion to the second portion to form the multi-part skin care bar.

A12.1. The multi-part skin care bar of paragraph A12, wherein the first engagement portion and the second engagement portion comprise complementary halves of one or more of a mortise and tenon joint, a rabbit joint, a miter joint, a biscuit joint, a dovetail joint, a tongue and groove joint, and a dowel joint.

A13. The multi-part skin care bar of any of paragraphs A12-A12.1, wherein the first engagement portion comprises a first projection extending from a first surface of the first portion.

A14. The multi-part skin care bar of any of paragraphs A12-A13, wherein the first engagement portion comprises at least two first projections extending from a/the first surface of the first portion.

A15. The multi-part skin care bar of any of paragraphs A12-A14, wherein the first engagement portion comprises a first receiving hole extending from a/the first surface of the first portion into a body of the first portion and towards a second surface of the first portion, the second surface of the first portion being opposite the first surface of the first portion.

A16. The multi-part skin care bar of any of paragraphs A12-A15, wherein the first engagement portion comprises at least two first receiving holes extending from a/the first surface of the first portion into a/the body of the first portion and towards a/the second surface of the first portion, the second surface of the first portion being opposite the first surface of the first portion.

A17. The multi-part skin care bar of any of paragraphs A12-A16, wherein the first engagement portion comprises at least one first projection and at least one first receiving hole, the at least one first projection extending from a/the first surface of the first portion and the at least one first receiving hole extending from the first surface of the first portion into a/the body of the first portion and towards a/the second surface of the first portion, the second surface of the first portion being opposite the first surface of the first portion.

A18. The multi-part skin care bar of any of paragraphs A12-A17, wherein the second engagement portion comprises a second projection extending from a first surface of the second portion, which may also be referred to herein as a third surface.

A19. The multi-part skin care bar of any of paragraphs A12-A18, wherein the second engagement portion comprises at least two second projections extending from a/the first surface of the second portion.

A20. The multi-part skin care bar of any of paragraphs A12-A19, wherein the second engagement portion comprises a second receiving hole extending from a/the first surface of the second portion into a body of the second portion and towards a second surface of the second portion, the second surface of the second portion being opposite the first surface of the second portion, the second surface also referred to herein as a fourth surface.

A21. The multi-part skin care bar of any of paragraphs A12-A20, wherein the second engagement portion comprises at least two second receiving holes extending from a/the first surface of the second portion into a/the body of the second portion and towards a/the second surface of the second portion, the second surface of the second portion being opposite the first surface of the second portion.

A22. The multi-part skin care bar of any of paragraphs A12-A21, wherein the second engagement portion comprises at least one second projection and at least one second receiving hole, the at least one second projection extending from a/the first surface of the second portion and the at least one second receiving hole extending from the first surface of the second portion into a/the body of the second portion and towards a/the second surface of the second portion, the second surface of the second portion being opposite the first surface of the second portion.

A22.1. The multi-part skin care bar of any of paragraphs A12-A22, wherein a/the first projection extending from a/the first surface of the first portion is configured to be inserted into a/the second receiving hole of the second portion, the second receiving hole extending from a/the first surface of the second portion and into a/the body of the second portion, towards a/the second surface of the second portion.

A22.2. The multi-part skin care bar of any of paragraphs A12-A22.1, wherein a/the second projection extending from a/the first surface of the second portion is configured to be inserted into a/the first receiving hole of the first portion, the first receiving hole extending from a/the first surface of the first portion and into a/the body of the first portion, towards a/the second surface of the first portion.

A22.3. The multi-part skin care bar of any of paragraphs A12-A22.2, wherein a first diameter of a/the first projection of the first engagement portion is approximately equal to a second diameter of a/the second receiving hole of the second engagement portion.

A22.4. The multi-part skin care bar of any of paragraphs A12-A22.2, wherein a first diameter of a/the first projection of the first engagement portion is greater than a second diameter of a/the second receiving hole of the second engagement portion.

A22.5. The multi-part skin care bar of any of paragraphs A12-A22.4, wherein a third diameter of a/the second projection of the second engagement portion is approximately equal to a fourth diameter of a/the first receiving hole of the first engagement portion.

A22.6. The multi-part skin care bar of any of paragraphs A12-A22.4, wherein a third diameter of a/the second projection of the second engagement portion is greater than a fourth diameter of a/the first receiving hole of the first engagement portion.

A23. The multi-part skin care bar of any of paragraphs A1-A22.6, wherein a/the second surface of the first portion is substantially flat.

A24. The multi-part skin care bar of any of paragraphs A1-A23, wherein a/the second surface of the second portion is substantially flat.

A25. The multi-part skin care bar of any of paragraphs A1-A24, wherein a/the first surface of the first portion is substantially flat, except in the area of a/the first engagement portion, the first engagement portion being configured to engage with a/the second engagement portion of the second portion to thereby couple the first portion to the second portion.

A26. The multi-part skin care bar of any of paragraphs A1-A25, wherein a/the first surface of the second portion is substantially flat, except in the area of a/the second engagement portion, the second engagement portion being configured to engage with a/the first engagement portion of the first portion to thereby couple the first portion to the second portion.

A27. The multi-part skin care bar of any of paragraphs A1-A24, wherein a/the first surface of the first portion has a first three-dimensional contoured shape, the first engagement portion being configured to engage with a/the second engagement portion of the second portion to thereby couple the first portion to the second portion.

A28. The multi-part skin care bar of paragraph A27, wherein a/the first surface of the second portion has a second three-dimensional contoured shape, the second engagement portion being configured to engage with the first engagement portion of the first portion to thereby couple the first portion to the second portion, wherein the first three-dimensional contoured shape and the second three-dimensional contoured shape are configured to be complementary, such that when the first portion and the second portion are coupled together, the first surface of the second portion and the first surface of the first portion form a smooth interface therebetween.

A29. The multi-part skin care bar of any of paragraphs A1-A28, wherein a/the first surface of the second portion comprises a plurality of first teeth extending therefrom, the plurality of first teeth being configured to engage a/the first surface of the first portion.

A30. The multi-part skin care bar of any of paragraphs A1-A29, wherein a/the first surface of the first portion comprises a plurality of second teeth extending therefrom, the plurality of second teeth being configured to engage a/the first surface of the second portion.

A31. The multi-part skin care bar of any of paragraphs A1-A30, wherein a/the first engagement portion of the first portion comprises the same material as the first portion, wherein the first engagement portion is configured to couple the first portion to the second portion.

A32. The multi-part skin care bar of any of paragraphs A1-A31, wherein a/the second engagement portion of the second portion comprises the same material as the second portion, wherein the second engagement portion is configured to couple the first portion to the second portion.

A33. The multi-part skin care bar of any of paragraphs A1-A32, wherein a/the second surface of the second portion comprises a plurality of scrubber attachments extending therefrom, the scrubber attachments being configured to be used on a user's skin.

A34. The multi-part skin care bar of any of paragraphs A1-A33, wherein the second portion comprises a notched hole extending from a/the first surface of the second portion to a/the second surface of the second portion.

A35. The multi-part skin care bar of any of paragraphs A1-A34 wherein a/the first engagement portion is formed integrally with the first portion, wherein the first engagement portion is configured to couple the first portion to the second portion.

A36. The multi-part skin care bar of any of paragraphs A1-A35, wherein a/the second engagement portion is formed integrally with the second portion, wherein the second engagement portion is configured to couple the first portion to the second portion.

A37. The multi-part skin care bar of any of paragraphs A1-A36, wherein a/the plurality of first portions comprises a plurality of varieties of soap, and wherein a/the plurality of second portions comprises a plurality of varieties of pumice soaps, wherein each of the plurality of first portions are substitutable for each other, and wherein each of the plurality of second portions are substitutable for each other, such that any respective first portion of the plurality of first portions is configured to be coupled to any respective second portion of the plurality of second portions.

B1. A system, comprising:
a plurality of first portions of a multi-part skin care bar, each of the plurality of first portions comprising a first engagement portion; and
a plurality of second portions of a multi-part skin care bar, each of the plurality of second portions comprising a second engagement portion, each of the plurality of second portions being configured to be coupled to a respective one of the plurality of first portions via the first engagement portion and the second engagement portion to form the multi-part skin care bar.

B2. The system of paragraph B1, wherein each of the plurality of first portions comprises soap.

B3. The system of any of paragraphs B1-B2, wherein the plurality of first portions comprises a plurality of types of soap that differ in one or more ways between one or more respective first portions of the plurality of first portions, optionally differing in one or more of ingredient, scent, and degree of moisturization.

B4. The system of any of paragraphs B1-B3, wherein at least some of the plurality of second portions comprise pumice.

B5. The system of any of paragraphs B1-B4, wherein at least some of the plurality of second portions comprise plastic.

B6. The system of any of paragraphs B1-B5, wherein at least some of the plurality of second portions comprise an elongate handle.

B7. The system of any of paragraphs B1-B6, wherein each of at least some of the plurality of second portions comprises a plurality of scrubber projections extending from a second surface of the respective second portion, wherein the second engagement portion of each respective second portion is positioned on a first surface of the respective second portion, wherein the first surface of the second portion is opposite the second surface of the second portion.

B8. The system of any of paragraphs B1-B7, wherein the first engagement portion of each of the plurality of first portions comprises a first projection extending from a first surface of each respective first portion, and wherein each respective first engagement portion comprises a first receiving hole extending from the first surface of each respective first portion and into a first body of the respective first portion, towards a second surface of the respective first portion, the second surface of each of the plurality of first portions being opposite the first surface of the respective first portion.

B9. The system of any of paragraphs B1-B8, wherein each respective second engagement portion comprises a second projection extending from a/the first surface of each respective second portion, and wherein each respective second engagement portion comprises a second receiving hole extending from the first surface of the respective second portion and into a second body of the respective second portion, towards a/the second surface of the respective second portion, the second surface of the respective second portion being opposite the first surface of the respective second portion.

B10. The system of any of paragraphs B1-B9, further comprising a plurality of cover elements, each cover element being configured to be coupled to a respective second portion of the plurality of second portions, and each cover element being configured to cover a respective first portion of the plurality of first portions, when the respective first portion is coupled to the respective second portion.

B11. The system of any of paragraphs B1-B10, wherein the plurality of first portions and the plurality of second portions are configured to form a plurality of multi-part skin care bars according to any of paragraphs A1-A37.

C1. A method, comprising:
providing a plurality of first portions of a multi-part skin care bar, the first portions comprising a first material; and
providing a plurality of second portions of a multi-part skin care bar, the second portions comprising a second material, the second material being different from the first material, wherein each respective first portion is configured to have a complementary shape to each respective second portion, wherein the first portions and the second portions are configured such that each respective first portion is configured to engage with a respective second portion.

C2. The method of paragraph C1, wherein the providing the plurality of first portions comprises offering to sell the plurality of first portions.

C3. The method of any of paragraphs C1-C2, wherein the providing the plurality of second portions comprises offering to sell the plurality of second portions.

C4. The method of any of paragraphs C1-C3, further comprising displaying information instructing a user to engage a respective first portion together with a respective second portion.

C5. The method of any of paragraphs C1-C4, further comprising providing instructions to a user regarding coupling a respective first portion to a respective second portion.

C6. The method of paragraph C5, wherein the providing instructions comprises one or more of providing written instructions, providing verbal instructions, and providing illustrated instructions.

C7. The method of any of paragraphs C1-C6, wherein the providing the plurality of first portions comprises providing a plurality of first portions, wherein one or more of the respective first portions comprises soap.

C8. The method of any of paragraphs C1-C7, wherein the providing the plurality of second portions comprises providing a plurality of second portions, wherein one or more of the respective second portions comprises pumice.

C9. The method of any of paragraphs C1-C8, wherein the providing the plurality of second portions comprises providing a plurality of second portions, wherein one or more of the respective second portions comprises plastic.

C10. The method of any of paragraphs C1-C9, wherein the providing the plurality of first portions comprises providing a plurality of first portions, wherein one or more of the plurality of first portions comprises a first variant, and wherein one or more of the plurality of first portions comprises a second variant, the first variant being different from the second variant.

C11. The method of any of paragraphs C1-C10, wherein the providing the plurality of first portions comprises providing a plurality of first portions, wherein each of the plurality of first portions comprises a respective scent, wherein a respective one or more of the plurality of first portions has a respective first scent, wherein a respective one or more of the plurality of first portions has a respective second scent, and wherein the respective first scent is different from the respective second scent.

C12. The method of any of paragraphs C1-C11, wherein the providing the plurality of second portions comprises providing a plurality of second portions, wherein a respective one or more of the plurality of second portions comprises pumice and another respective one or more of the plurality of second portions comprises plastic.

C13. The method of any of paragraphs C1-C12, wherein the providing the plurality of second portions comprises providing a plurality of second portions, wherein a respective one or more of the plurality of second portions comprises an elongate scrubber.

C14. The method of any of paragraphs C1-C13, wherein the providing the plurality of first portions and the providing the plurality of second portions comprises providing a plurality of multi-part skin care bars, each of the plurality of multi-part skin care bars being a multi-part skin care bar according to any of paragraphs A1-A37.

C15. The method of any of paragraphs C1-C14, wherein the providing the plurality of first portions comprises selling the plurality of first portions individually, and wherein the providing the plurality of second portions comprises selling the plurality of second portions individually.

D1. A method, comprising:
selling a kit, the kit comprising one or more first portions and one or more second portions, each respective first portion being configured to be coupled to a respective second portion via complementary features formed on and/or in the first portion and the second portion, wherein coupling a respective first portion to a respective second portion forms a multi-part skin care bar; and
providing instructions for coupling a respective first portion to a respective second portion.

D2. The method of paragraph D1, wherein the selling the kit comprises selling the kit, wherein the kit is configured to form the multi-part skin care bar of any of paragraphs A1-A37.

D3. The method of any of paragraphs D1-D2, wherein the providing the instructions for coupling a respective first portion to a respective second portion comprises providing instructions to insert a/the first projection extending from the first portion into a/the second receiving hole formed within the second portion, and to insert a/the second projection extending from the second portion into a/the first receiving hole formed within the first portion.

D4. The method of any of paragraphs D1-D3, wherein the kit comprises a plurality of first portions and one second portion, wherein each of the plurality of first portions comprises soap, and wherein the second portion comprises pumice.

D5. The method of any of paragraphs D1-D4, wherein the kit comprises a plurality of first portions, wherein the plurality of first portions comprise a plurality of varieties of soap, wherein the kit comprises a single second portion, and wherein the single second portion is configured to be reusable such that it may be used with each of the plurality of first portions.

D6. The method of any of paragraphs D1-D5, wherein the complementary features formed on and/or in the first portion and the second portion comprise a first engagement portion of the first portion and a second engagement portion of the second portion.

D7. The method of paragraph D6, wherein the first portion comprises soap, wherein the first engagement portion is formed integrally with the first portion, wherein the second portion comprises one or more of pumice and plastic, and wherein the second engagement portion is formed integrally with the second portion.

E1. A method of using a multi-part skin care bar, the method comprising:
selecting a first portion of the multi-part skin care bar;
selecting a second portion of the multi-part skin care bar; and
forming the multi-part skin care bar by coupling the first portion to the second portion.

E2. The method of paragraph E1, further comprising using the multi-part skin care bar to clean a portion of a user's body.

E3. The method of any of paragraphs E1-E2, further comprising using the multi-part skin care bar to exfoliate a portion of a user's body.

E4. The method of any of paragraphs E1-E3, further comprising using the multi-part skin care bar to scrub a portion of a user's body.

E5. The method of any of paragraphs E1-E4, wherein the selecting the first portion comprises selecting the first portion from a plurality of first portions.

E6. The method of any of paragraphs E1-E5, wherein the selecting the second portion comprises selecting the second portion from a plurality of second portions.

E7. The method of any of paragraphs E1-E6, wherein the selecting the first portion comprises selecting a first portion having moisturizing and/or cleansing properties.

E8. The method of any of paragraphs E1-E7, wherein the selecting the second portion comprises selecting a second portion having scrubbing and/or exfoliating properties.

E9. The method of any of paragraphs E1-E8, wherein the forming the multi-part skin care bar comprises forming the multi-part skin care bar of any of paragraphs A1-A37.

E10. The method of any of paragraphs E1-E9, wherein the forming the multi-part skin care bar comprises inserting a/the first projection of the first portion into a/the second receiving hole of the second portion and inserting a/the second projection of the second portion into a/the first receiving hole of the first portion, thereby coupling the first portion to the second portion.

F1. A first portion of a multi-part skin care bar, the first portion comprising:
 a first body comprising soap, and being configured to be used to clean a user's skin;
 a first surface of the first portion, wherein the first surface of the first portion is substantially flat;
 a second surface of the first portion opposite the first surface of the first portion, wherein the second surface of the first portion comprises a three-dimensional contoured surface;
 a first projection extending from the second surface of the first portion; and
 a first receiving hole extending into the first body from the second surface of the first portion and towards the first surface of the first portion, wherein the first receiving hole is configured to receive a second projection extending from a second portion of the multi-part skin care bar, and wherein the first portion is configured to be coupled to the second portion to form the multi-part skin care bar.

F2. The first portion of paragraph F1, wherein the first projection comprises soap.

F3. The first portion of any of paragraphs F1-F2, wherein the first projection comprises a first cylindrical projection.

F4. The first portion of any of paragraphs F1-F3, wherein the first projection comprises a plurality of first projections.

F5. The first portion of any of paragraphs F1-F4, wherein the first receiving hole comprises a plurality of first receiving holes.

G1. A second portion of a multi-part skin care bar, the second portion comprising:
 a second body comprising pumice, and being configured to be used to exfoliate and/or scrub a user's skin;
 a first surface of the second portion, wherein the first surface of the second portion is substantially flat;
 a second surface of the second portion opposite the first surface of the second portion, wherein the second surface of the second portion comprises a three-dimensional contoured surface;
 a second projection extending from the second surface of the second portion; and
 a second receiving hole extending into the second body from the second surface of the second portion and towards the first surface of the second portion, wherein the second receiving hole is configured to receive a first projection extending from a first portion of the multi-part skin care bar, and wherein the second portion is configured to be coupled to the first portion to form the multi-part skin care bar.

G2. The second portion of paragraph G1, wherein the second projection comprises pumice.

G3. The second portion of any of paragraphs G1-G2, wherein the second projection comprises a second cylindrical projection.

G4. The second portion of any of paragraphs G1-G3, wherein the second projection comprises a plurality of second projections.

G5. The second portion of any of paragraphs G1-G4, wherein the second receiving hole comprises a plurality of second receiving holes.

H1. A multi-part skin care bar, comprising:
 the first portion of any of paragraphs F1-F5; and
 the second portion of any of paragraphs G1-G5, wherein the first projection is configured to be inserted into the second receiving hole and the second projection is configured to be inserted into the first receiving hole, thereby coupling the first portion to the second portion to form the multi-part skin care bar.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A multi-part skin care bar, comprising:
a first portion comprising a first body comprising a first soap, the first portion comprising a first surface and a second surface opposite the first surface, wherein the first surface comprises a first engagement portion, wherein the first engagement portion comprises at least one first member selected from the group consisting of a first peg extending from the first surface and a first receiving hole extending from the first surface into the first body and towards the second surface, wherein the first engagement portion is integrally formed with the first portion, and wherein the first engagement portion is formed of or in the first soap; and
a second portion comprising a second body comprising at least one material selected from the group consisting of a second soap different from the first soap, pumice, and plastic, the second portion comprising a third surface and a fourth surface opposite the third surface, wherein the third surface comprises a second engagement portion, wherein the second engagement portion comprises at least one second member selected from the group consisting of a second peg extending from the third surface and a second receiving hole extending from the third surface into the second body and towards the fourth surface, wherein the second engagement portion is integrally formed with the second portion, wherein the second engagement portion is formed of or in the at least one material, and wherein the first portion and the second portion are configured to be coupled together via the first engagement portion and the second engagement portion to form the multi-part skin care bar.

2. The multi-part skin care bar according to claim 1, wherein the first portion comprises a plurality of first portions, the second portion comprises a plurality of second portions, and wherein each respective first portion of the plurality of first portions is configured to engage with any respective second portion of the plurality of second portions.

3. The multi-part skin care bar according to claim 2, wherein the plurality of first portions comprises a plurality of varieties of soap, and wherein the plurality of second portions comprises a plurality of varieties of pumice soaps, wherein each of the plurality of first portions are substitutable for each other, and wherein each of the plurality of second portions are substitutable for each other, such that any respective first portion of the plurality of first portions is configured to be coupled to any respective second portion of the plurality of second portions.

4. The multi-part skin care bar according to claim 1, wherein the first portion and the second portion are identical in size and shape.

5. The multi-part skin care bar according to claim 1, wherein the second portion comprises an elongate scrubber, the elongate scrubber having an elongate handle extending from a receiving portion, the receiving portion being configured to engage with the first portion.

6. The multi-part skin care bar according to claim 1, wherein the first engagement portion comprises at least one first peg extending from the first surface and at least one first receiving hole extending from the first surface into the first body and towards the second surface.

7. The multi-part skin care bar according to claim 6, wherein the second engagement portion comprises at least one second peg and at least one second receiving hole, the at least one second peg extending from the third surface and the at least one second receiving hole extending from the third surface into the second body and towards the fourth surface.

8. The multi-part skin care bar according to claim 7, wherein the first peg extending from the first surface of the first portion is configured to be inserted into the second receiving hole of the second portion, and wherein the second peg extending from the third surface of the second portion is configured to be inserted into the first receiving hole of the first portion.

9. The multi-part skin care bar according to claim 1, wherein the second surface of the first portion and the fourth surface of the second portion are flat.

10. The multi-part skin care bar according to claim 1, wherein the first surface of the first portion has a first three-dimensional contoured shape, the third surface of the second portion has a second three-dimensional contoured shape, wherein the first three-dimensional contoured shape and the second three-dimensional contoured shape are configured to be complementary, such that when the first portion and the second portion are coupled together, the third surface of the second portion and the first surface of the first portion form a smooth interface therebetween.

11. The multi-part skin care bar according to claim 1, wherein the third surface of the second portion comprises a plurality of gripping features extending therefrom, the plurality of gripping features being configured to engage the first surface of the first portion.

12. The multi-part skin care bar according to claim 11, wherein the fourth surface of the second portion comprises a plurality of scrubber attachments extending therefrom, the scrubber attachments being configured to be used on a user's skin.

13. The multi-part skin care bar according to claim 12, wherein the second portion comprises a notched hole extending from the third surface of the second portion to the fourth surface of the second portion, the notched hole being configured to receive at least a portion of the first engagement portion of the first portion.

14. A first portion of a multi-part skin care bar, the first portion comprising:
a first body comprising soap, and being configured to be used to clean a user's skin;
a first surface of the first portion;
a second surface of the first portion opposite the first surface of the first portion, wherein the second surface of the first portion comprises a three-dimensional contoured surface;
a first peg extending from the second surface of the first portion, wherein the first peg is integrally formed with the first portion, and wherein the first peg comprises soap; and
a first receiving hole extending into the first body from the second surface of the first portion and towards the first surface of the first portion, wherein the first receiving hole is integrally formed with the first portion, wherein the first receiving hole is formed in soap; wherein the first receiving hole is configured to receive a second peg extending from a second portion of the multi-part skin care bar, wherein the first peg is configured to be inserted into a second receiving hole of the second portion, and wherein the first portion is configured to be coupled to the second portion to form the multi-part skin care bar, via the first receiving hole receiving the first peg, and via the second receiving hole receiving the second peg.

15. The multi-part skin care bar according to claim 1, wherein the at least one material comprises the second soap.

16. The multi-part skin care bar according to claim 1, wherein the at least one material comprises pumice.

17. The multi-part skin care bar according to claim 1, wherein the at least one material comprises plastic.

18. The multi-part skin care bar according to claim 1, wherein the first portion and the second portion are configured to be selectively and removably coupled together to form the multi-part skin care bar.

19. A multi-part skin care bar, comprising:
a first portion comprising a first body formed of a first material, wherein the first material comprises soap, the first portion comprising a first surface and a second surface opposite the first surface, wherein the first surface comprises a first engagement portion, wherein the first engagement portion comprises at least one first member selected from the group consisting of a first peg extending from the first surface and a first receiving hole extending from the first surface into the first body and towards the second surface, wherein the first engagement portion is integrally formed with the first portion, and wherein the first engagement portion is formed of or in the first material; and
a second portion comprising a second body formed of a second material, wherein the second material is different from the first material, wherein the second portion comprises a third surface and a fourth surface opposite the third surface, wherein the third surface comprises a second engagement portion, wherein the second engagement portion comprises at least one second member selected from the group consisting of a second peg extending from the third surface and a second receiving hole extending from the third surface into the second body and towards the fourth surface, wherein the second engagement portion is integrally formed with the second portion, wherein the second engagement portion is formed of or in the second material, and wherein the first portion and the second portion are configured to be coupled together by engaging the first engagement portion and the second engagement portion to form the multi-part skin care bar.

* * * * *